(12) United States Patent
Levi et al.

(10) Patent No.: US 8,402,970 B2
(45) Date of Patent: Mar. 26, 2013

(54) SYSTEM AND METHOD FOR INTEGRATED HIGH FREQUENCY OSCILLATORY VENTILATION

(75) Inventors: Andrew Phillip Levi, Madison, WI (US); Robert Edwin Braatz, Sun Prairie, WI (US)

(73) Assignee: General Electric Company, Schenectady, NY (US)

( * ) Notice: Subject to any disclaimer, the term of this patent is extended or adjusted under 35 U.S.C. 154(b) by 1411 days.

(21) Appl. No.: 12/048,312

(22) Filed: Mar. 14, 2008

(65) Prior Publication Data

US 2009/0229612 A1 Sep. 17, 2009

(51) Int. Cl.
*A61M 16/00* (2006.01)

(52) U.S. Cl. ......... 128/205.19; 128/200.24; 128/204.18; 128/204.21

(58) Field of Classification Search ............. 128/200.24, 128/204.18, 204.21, 204.25, 205.11, 205.19
See application file for complete search history.

(56) References Cited

U.S. PATENT DOCUMENTS

| | | | |
|---|---|---|---|
| 3,923,055 A | 12/1975 | Hammacher | |
| 4,409,977 A * | 10/1983 | Bisera et al. ............. | 128/205.15 |
| 4,463,756 A * | 8/1984 | Thuc ........................ | 128/204.21 |
| 4,543,951 A * | 10/1985 | Phuc ........................ | 128/204.25 |
| 4,596,247 A * | 6/1986 | Whitwam et al. ........ | 128/204.25 |
| 5,239,994 A | 8/1993 | Atkins | |
| 5,423,313 A * | 6/1995 | Olsson et al. ............. | 128/204.21 |
| 5,522,381 A * | 6/1996 | Olsson et al. ............. | 128/203.12 |
| 5,555,880 A * | 9/1996 | Winter et al. ............. | 128/204.21 |
| 5,954,050 A * | 9/1999 | Christopher ............. | 128/204.23 |
| 6,095,138 A * | 8/2000 | Hognelid et al. ......... | 128/204.18 |
| 6,581,600 B2 | 6/2003 | Bird | |
| 6,595,213 B2 * | 7/2003 | Bennarsten ............... | 128/205.19 |
| 6,640,807 B2 * | 11/2003 | Bennarsten ............... | 128/205.24 |
| 7,198,679 B2 * | 4/2007 | Hallback et al. ......... | 128/204.23 |
| 7,861,716 B2 * | 1/2011 | Borrello ................... | 128/204.21 |

FOREIGN PATENT DOCUMENTS

EP 0234736 1/1993

* cited by examiner

*Primary Examiner* — Annette Dixon

(57) ABSTRACT

An integrated ventilation system is presented. The integrated ventilation system includes a high frequency ventilation module configured to be operationally coupled to a ventilation system, where the high frequency ventilation module is configured to aid the ventilation system in performing high frequency ventilation. A method for providing high frequency ventilation via use of a high frequency ventilation module, where the high frequency ventilation module is configured to be operationally coupled to a ventilation system, and where the high frequency ventilation module is configured to aid the ventilation system in performing high frequency ventilation, is presented. The method includes creating a vacuum effect at an outlet port of the ventilation system to aid in active exhalation of gas from a patient.

19 Claims, 3 Drawing Sheets

SYSTEM AND METHOD FOR INTEGRATED HIGH FREQUENCY OSCILLATORY VENTILATION

BACKGROUND

Figure 1:
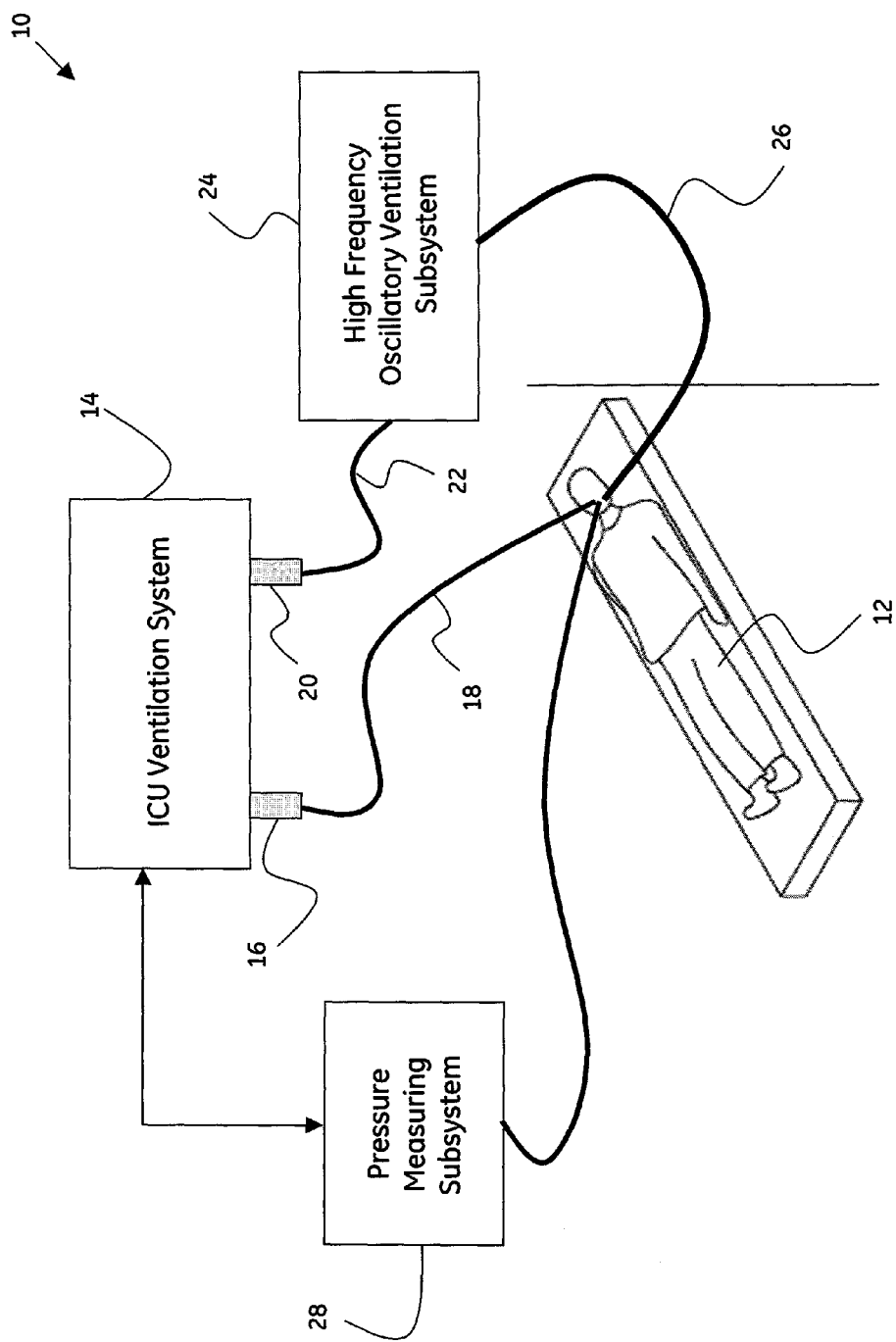

This disclosure relates generally to clinical workflow, and more particularly to a design of a device configured to aid in enhancing clinical workflow.

In a caregiving facility, such as a hospital, and more particularly, in an Intensive Care Unit (ICU), it may be desirable to provide artificial ventilation to one or more patients. As will be appreciated, patients in the ICU that have been identified as needing artificial ventilation are typically intubated and ventilated in order to treat and manage respiratory failures, such as asthma, pneumonia, pulmonary edema, pulmonary embolism, chronic bronchitis, post-operative hypoxemia, chest injuries and chronic lung disease. Along with patients suffering from respiratory failure, certain patients may need ventilatory support for other medical reasons. By way of example, post-operative ICU patients and certain maxillofacial surgical patients may also require a period of post operative care in the ICU, during which time the patients are typically kept sedated and ventilated.

Traditionally, artificial ventilation is provided via use of a ventilator. More particularly, artificial ventilation is provided via positive pressure ventilation, where gas is delivered under positive pressure, allowing alveoli expansion and gas exchange. Once a patient has been identified as needing artificial ventilation, they are intubated and placed on a ventilator and ventilated using positive pressure. Gases are delivered to the patient using pressure to inflate the lungs, expand the alveoli and allow for gas exchange and oxygenation. In other words, one of the goals of conventional artificial ventilation is to use positive pressure to deliver gas and achieve respective ventilatory goals.

However, the effects of this non-physiological approach to ventilation are numerous and can be detrimental. Furthermore, in diseased lungs, positive pressure ventilation may not always provide adequate carbon dioxide ($CO_2$) clearance or oxygen delivery and may even result in alveolar and/or lung damage due to ventilating at high airway pressures. The other side effects of positive pressure ventilation may include decreased cardiac output, reduced venous return, decreased urine output, retention of fluids, risk of ventilator associated pneumonia, and risk of tracheal and lung damage if gases are not humidified.

An alternative approach to conventional ventilation has emerged over the last decade and is known as High Frequency Ventilation. It may be noted that High Frequency Ventilation may include High Frequency Oscillatory Ventilation (HFOV). Patients, who are at risk of further lung damage due to increases in airway pressure secondary to increases in resistance and decreases in compliance, may benefit from HFOV. In other words, when conventional ventilation fails to safely and adequately provide respiratory support, HFOV may be considered as an alternative method of ventilating the patient.

As will be appreciated, HFOV provides small tidal volumes usually equal to, or less than the dead space (e.g., about 2 ml/kg), at a very fast rate of between 5-15 breaths per second. The delivery of tidal volumes of dead space or less at very high frequencies enables the maintenance of a minute volume. Furthermore, lungs are kept open to a constant airway pressure via a mean pressure adjust system. Also, HFOV advantageously allows for the decoupling of oxygenation from ventilation as HFOV allows the clinician to separately adjust either oxygenation or ventilation.

As noted hereinabove, HFOV is a specialized form of ventilation considered to be part of a lung protective strategy to ventilate a patient with damaged lungs. HFOV has traditionally been applied through the use of a device separate from the ICU ventilator, where the ICU ventilator is typically used to assist patients that are unable to breathe on their own. However, use of the standalone HFOV ventilator has huge cost implications. Moreover, a transition between normal ventilation via use of the ICU ventilator and HFOV via the HFOV ventilator may unfortunately result in loss of pressure in the lungs of the patient, thereby causing discomfort to the patient. Moreover, there are equipment, time, and training issues associated with having the HFOV function separate from the ICU ventilator.

It may therefore be desirable to develop a design of a system that may be configured to advantageously aid the ICU ventilator in performing HFOV, thereby enhancing the clinical workflow by reducing equipment size, time to apply HFOV and reducing cost. More particularly, it may be desirable to provide seamless transition between normal ICU ventilation and HFOV, thereby preventing loss of circuit pressure during the transition and minimizing discomfort to the patient.

BRIEF DESCRIPTION

In accordance with aspects of the present technique, an integrated ventilation system is presented. The integrated ventilation system comprises a high frequency ventilation module configured to be operationally coupled to a ventilation system, where the high frequency ventilation module is configured to aid the ventilation system in performing high frequency ventilation.

In accordance with further aspects of the present technique, an integrated ventilation system is presented. The integrated ventilation system includes a ventilation system configured to provide artificial respiration to a patient. In addition, the integrated ventilation system also includes a high frequency ventilation module configured to be operationally coupled to the ventilation system, where the high frequency ventilation module is configured to aid the ventilation system in performing high frequency ventilation.

In accordance with further aspects of the present technique, a method for providing high frequency ventilation via use of a high frequency ventilation module, where the high frequency ventilation module is configured to be operationally coupled to a ventilation system, and where the high frequency ventilation module is configured to aid the ventilation system in performing high frequency ventilation is presented. The method includes creating a vacuum effect at an outlet port of the ventilation system to aid in active exhalation of gas from a patient.

DRAWINGS

Figure 2:
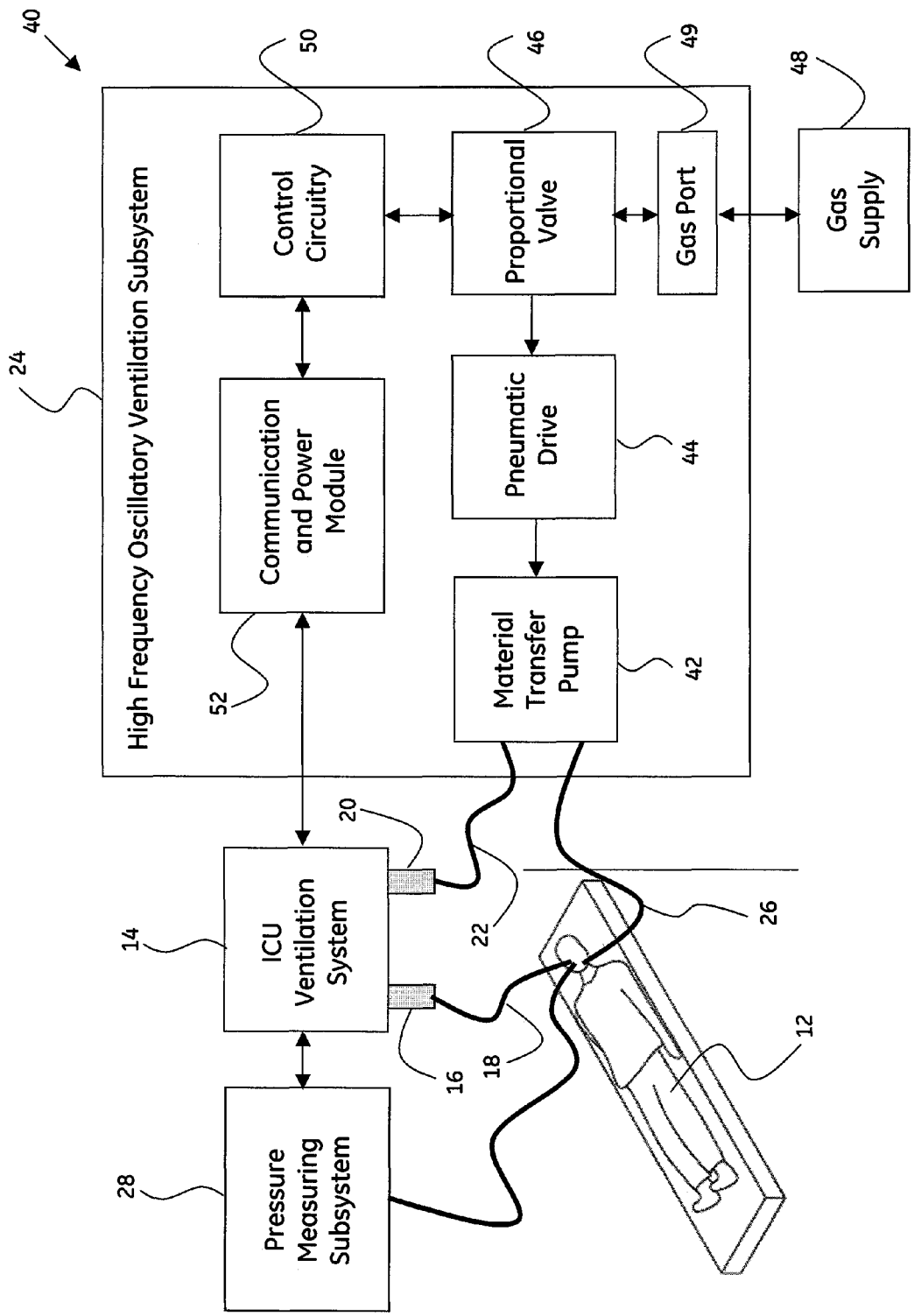
Figure 3:
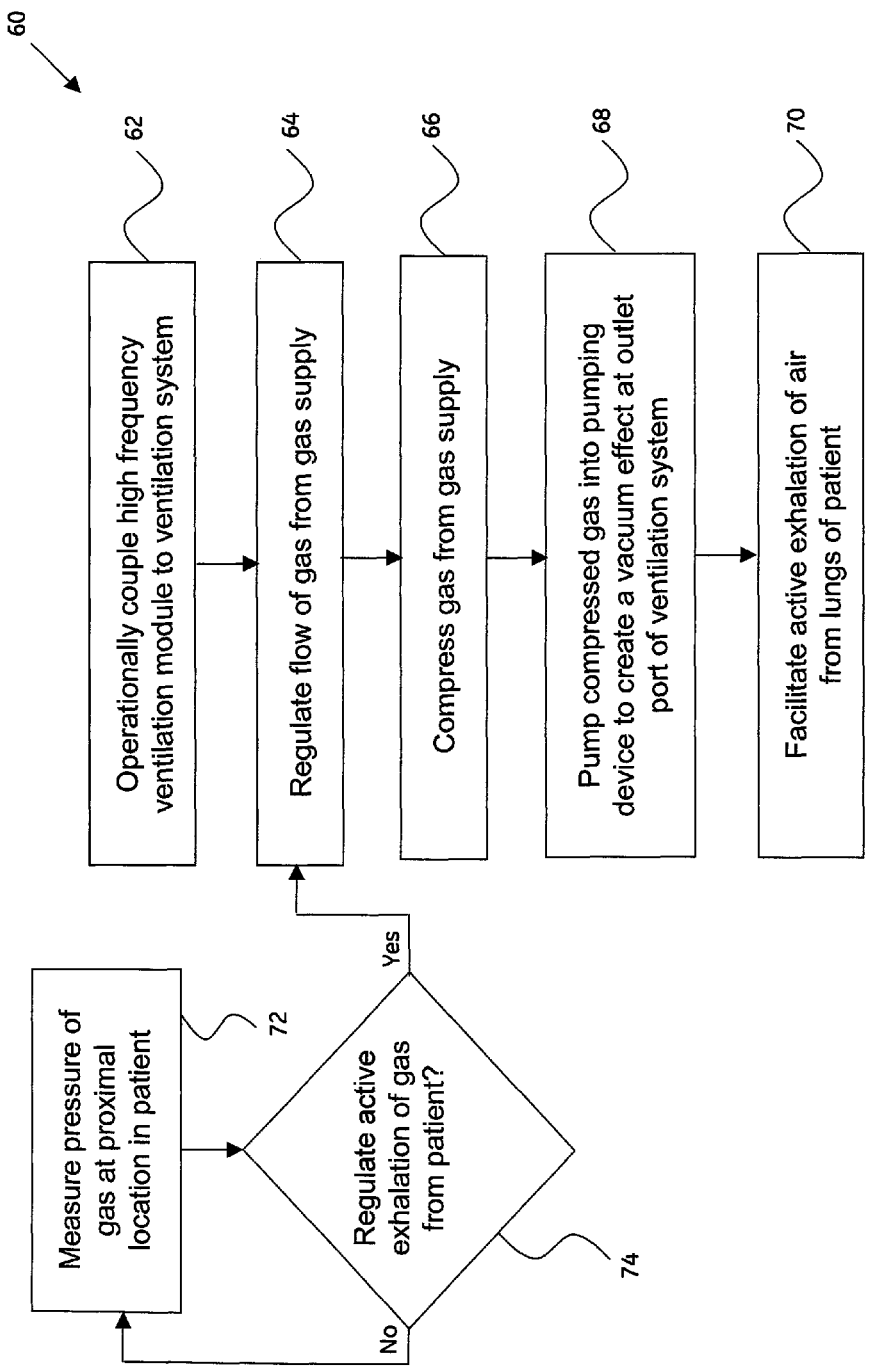

These and other features, aspects, and advantages of the present invention will become better understood when the following detailed description is read with reference to the accompanying drawings in which like characters represent like parts throughout the drawings, wherein:

FIG. 1 is a block diagram of an integrated high frequency oscillatory ventilation system, in accordance with aspects of the present technique;

FIG. 2 is a block diagram of an embodiment of the integrated high frequency oscillatory ventilation system of FIG. 1, in accordance with aspects of the present technique; and FIG. 3 is a flow chart illustrating an exemplary method for providing enhanced ventilation using the exemplary integrated high frequency oscillatory ventilation system of FIG. 1, in accordance with aspects of the present technique.

DETAILED DESCRIPTION

FIG. 1 is a block diagram of an exemplary integrated high frequency oscillatory ventilation (HFOV) system 10, in accordance with aspects of the present technique. More particularly, the system 10 may be configured to aid in providing integrated ventilation to a patient 12. In other words, the exemplary integrated HFOV system 10 may be configured to aid a traditional ICU ventilator in performing HFOV, thereby enhancing clinical workflow by providing seamless transition between normal ICU ventilation and HFOV, and preventing loss of circuit pressure during the transition and minimizing discomfort to the patient 12.

As previously noted, once a patient, such as the patient 12, has been identified as needing artificial ventilation, the patient 12 may be operationally coupled to a ventilation system 14. In a presently contemplated configuration, the ventilation system 14 may include a traditional ICU ventilation system. As will be appreciated, the ICU ventilation system 14 is a machine that may be configured to aid the patient 12 in breathing through a tube that is typically inserted into the trachea of the patient 12 via the mouth or nose of the patient 12, where the tube is operationally coupled to the ICU ventilation system 14. Further, the ICU ventilation system 14 may include an inlet port 16 and an outlet port 20. It may be noted that the terms "inlet" port and "outlet" port are named from the perspective of the patient 12. The patient 12 may be operationally coupled to the inlet port 16 of the ICU ventilation system 14 via an inlet tube 18. It may be noted that the inlet tube 18 may also be referred to as an inspiratory tube. The ICU ventilation system 14 may be configured to pump gas into the lungs of the patient 12 through the inlet port via use of the inlet tube 18.

The patient 12 may be operationally coupled to either the ICU ventilation system 14 or a separate HFOV system (not shown in FIG. 1), depending on severity of the lung damage of the patient 12, as previously noted. More particularly, HFOV is typically applied through the use of a device separate from the ICU ventilation system 14. However, use of two separate devices to provide artificial ventilation to the patient 12 may disadvantageously result in loss of circuit pressure during the transition, thereby causing discomfort to the patient 12. According to exemplary aspects of the present technique, a module configured to advantageously aid a traditional ICU ventilator, such as the ICU ventilation system 14, in performing HFOV, is presented. More particularly, a high frequency oscillatory ventilation (HFOV) subsystem 24 that may be configured to aid the ICU ventilation system 14 in performing HFOV is presented.

With continuing reference to FIG. 1, in one embodiment, the HFOV subsystem 24 may be operationally coupled to an outlet pathway of the ICU ventilation system 14. In a presently contemplated configuration, the HFOV subsystem 24 may be operationally coupled to the outlet port 20 of the ICU ventilation system 14. As will be appreciated, the outlet port 20 of the ICU ventilation system 14 may be configured to facilitate exhalation of gas from the lungs of the patient 12. In one embodiment, an input of the HFOV subsystem 24 may be coupled to the ICU ventilation system 14 via an outlet tube 22.

It may be noted that the outlet tube 22 may also be referred to as an expiratory tube. More particularly, an input of the HFOV subsystem 24 may be operationally coupled to the outlet port 20 of the ICU ventilation system 14 via the outlet tube 22. Moreover, an output of the HFOV subsystem 24 may be coupled to the patient 12 via a tube 26.

As will be appreciated, the ICU ventilation system 14 may be configured to pump gas into the patient 12. However, the ICU ventilation system 14 fails to aid the patient 12 in exhalation of air. In other words, the ICU ventilation system 14 is configured to wait for the patient 12 to passively exhale the air. The shortcomings of the traditional ICU ventilation system 14 may be circumvented via use of the HFOV subsystem 24. More particularly, the HFOV subsystem 24 may be configured to provide the ICU ventilation system 14 with an ability to actively suck out the gas from the lungs of the patient 12, thereby facilitating active exhalation of gas from the lungs of the patient 12. In other words, the HFOV subsystem 24 may be configured to aid the ICU ventilation system 14 in regulating gas being sucked out of the lungs of the patient 12 in an active fashion. The working of the HFOV subsystem 24 will be described in greater detail with reference to FIGS. 2-3. In addition, the system 10 may include a pressure measuring subsystem 28, where the pressure measuring subsystem 28 may be configured to aid in monitoring a pressure of gas that is pumped into the patient 12. More particularly, the pressure measuring subsystem 28 may be configured to monitor the pressure of gas at a proximal location in the patient 12.

Referring now to FIG. 2, one embodiment 40 of the HFOV subsystem 24 (see FIG. 1) is illustrated. As previously noted, an input of the HFOV subsystem 24 may be operationally coupled to the outlet port 20 of the ICU ventilation system 14 via the outlet tube 22. Further, an output of the HVOF subsystem 24 may be operationally coupled to the patient 12 via the tube 26.

Also, as previously noted with reference to FIG. 1, the HFOV subsystem 24 may be configured to aid the ICU ventilation system 14 in actively sucking out the gas from the lungs of the patient 12 by providing the system 10 (see FIG. 1) an ability to regulate gas being sucked out of the lungs of the patient 12 in an active fashion. Accordingly, in a presently contemplated configuration, the HFOV subsystem 24 may include a pumping device 42, where the pumping device 42 may be configured to aid in actively sucking the gas out of the lungs of the patient 12. In one embodiment, the pumping device 42 may include a material transfer pump. Furthermore, the HFOV subsystem 24 may also include a pneumatic drive 44, a proportional valve 46, a gas port 49, control circuitry 50, and a communication and power module 52.

The pumping device, such as the material transfer pump 42, may be configured to include a high flow vacuum pump (not shown in FIG. 2). The high flow vacuum pump may be configured to provide a reliable and cost effective method of in-line transfer of complex shapes and bulk materials such as small parts, continuous strips, and powders. Compressed air is fed into an exterior annular ring (not shown in FIG. 2) that has a number of orifices leading into a main tube of a transducer (not shown in FIG. 2). As the compressed air exits from the orifices, velocity of the compressed air increases to supersonic speed. The air forced into the center of the tube rotates with a twisting motion. This cyclonic flow creates a powerful vacuum capable of drawing materials into, and through the transducer.

In accordance with exemplary aspects of the present technique, the material transfer pump 42 may be employed to facilitate active exhalation of gas from the lungs of the patient 12. More particularly, the material transfer pump 42 may be configured to aid in creating a vacuum effect at the outlet port 20 of the ICU ventilation system 14, thereby facilitating active exhalation of gas from the lungs of the patient 12. As noted hereinabove, the material transfer pump 42 may include one or more orifices or cross-drilled holes in an exterior annular ring (not shown in FIG. 2). In addition, the system 40 may also include a gas supply 48, where the gas supply 48 may be configured to provide gas to be pumped into the material transfer pump 42. Although in the present embodiment, the gas supply 48 is shown as being separate from the HFOV subsystem 24, it may be noted that the gas supply 48 may be an integral part of the HFOV subsystem 24, in certain embodiments. The gas port 49 in the HFOV subsystem 24 may be configured to receive gas from the gas supply 48. It may be noted that vacuum flow rates may be controlled over an entire range of the material transfer pump 42 by regulating the input pressure of the gas. Accordingly, the proportional valve 46 may be configured to aid in controlling the vacuum flow rate at the outlet port 20 of the ICU ventilation system 14. In other words, the proportional valve 46 may be configured to regulate the input pressure of the gas from the gas supply 48 by increasing and/or decreasing the flow of gas from the gas supply 48 into the material transfer pump 42.

Furthermore, as noted hereinabove, compressed gas may be pumped into the material transfer pump 42 to aid in generating the vacuum effect at the outlet port 20 of the ICU ventilation system 14. In accordance with aspects of the present technique, the pneumatic drive 44 may be configured to compress the gas from the gas supply 48 to a desirable level. This compressed gas may then be pumped into the material transfer pump 42 to facilitate creation of the vacuum effect at the outlet port 20 of the ICU ventilation system 14. Accordingly, the pneumatic drive 44 may be configured to pump the gas from the gas supply 48 through the cross-drilled holes in the material transfer pump 42, thereby aiding in creating a negative pressure at the outlet port 20 of the ICU ventilation system 14. This negative pressure at the outlet port 20 of the ICU ventilation system 14 aids in the generation of a vacuum effect at the outlet port 20 of the ICU ventilation system 14. Furthermore, this vacuum effect at the outlet port 20 may be configured to facilitate sucking the gas out of the lungs of the patient 12. In other words, this sucking out of the gas from the lungs of the patient 12 enables active exhalation of gas from the lungs of the patient 12, as opposed to the typical passive exhalation of gas offered via use of the traditional ICU ventilators, such as the ICU ventilation system 14.

Moreover, the communication and power module 52 may be configured to aid in communication between the ICU ventilation system 14 and the HFOV subsystem 24. Additionally, the communication and power module 52 may also be configured to aid in providing power to the HFOV subsystem 24. As previously noted, the pressure measuring subsystem 28 may be configured to aid in measuring the pressure of the gas that is input into the patient 12 via the ICU ventilation system 14. Based on the measurements obtained by the pressure measuring subsystem 28, it may be desirable to regulate active exhalation of the gas from the lungs of the patient 12. Accordingly, the communication and power module 52 may be configured to communicate any desirable changes in the active exhalation of gas from the lungs of the patient 12 to the control circuitry 50, which in turn may be configured to regulate the proportional valve 46, thereby regulating the flow of gas from the gas supply 48 into the material transfer pump 42. Consequently, the vacuum effect at the outlet port 20 of the ICU ventilation system 14 may be regulated.

Traditionally, the inspiratory and expiratory tubes, such as the tubes 18, 22, coupling the patient 12 to the ICU ventilation system 14 include corrugated tubes. Unfortunately, use of corrugated tubes results in non-optimal gas flow in the tubes due to turbulence in the breathing circuits. In accordance with aspects of the present technique, the shortcomings of the traditional corrugated tubes may be circumvented via use of smooth bore tubes. The smooth bore breathing circuits may be configured to present substantially reduced resistance to the gas flow in the tubes, thereby enhancing the artificial ventilation of the patient 12 and reducing patient discomfort. Also, use of the smooth bore breathing circuits results in dramatically reduced costs.

By implementing the HFOV subsystem 24 as described hereinabove, the HFOV subsystem 24 may be configured to aid the ICU ventilation system 14 in performing HFOV, thereby reducing equipment size, cost and time to apply HFOV. In addition, seamless transition between normal ventilation via use of the traditional ICU ventilator and HFOV may be obtained, thereby substantially reducing loss of circuit pressure during the transition. Additionally, implementing the HFOV subsystem 24 as a standalone module advantageously aids in backward compatibility with existing ICU ventilators. Although the HFOV subsystem 24 is described hereinabove as a standalone module, it may be noted that the HFOV subsystem 24 may be integrated into the ICU ventilation system 14.

In accordance with yet another aspect of the present technique, a method for providing high frequency ventilation via use of a high frequency ventilation module is presented. FIG. 3 is a flow chart 60 illustrating an exemplary method for providing high frequency ventilation via use of a high frequency ventilation module. More particularly, a method configured to aid a traditional ICU ventilator, such as the ICU ventilation system 14 (see FIG. 1), in performing HFOV is presented.

The method starts at step 62, where an exemplary HFOV module, such as the HFOV subsystem 24 (see FIG. 1) may be operationally coupled to an ICU ventilator, such as the ICU ventilation system 14 (see FIG. 1). More particularly, the HFOV subsystem may be operationally coupled to an outlet port, such as the outlet port 20 (see FIG. 2) of the ICU ventilation system. Furthermore, as previously described with reference to FIG. 2, the HFOV subsystem 24 may be configured to include a pumping device, such as the material transfer pump 42 (see FIG. 2), where the material transfer pump may be configured to aid in creating a vacuum effect at the outlet port of the ICU ventilation system. Accordingly, flow of gas from a gas supply to the material transfer pump may be regulated, as indicated by step 64. It may be noted that vacuum flow rates may be controlled over an entire range of the material transfer pump by regulating the input pressure of the gas. In one embodiment, the flow of gas from the gas supply to the material transfer pump may be regulated via use of a proportional valve, such as the proportional valve 46 (see FIG. 2), as previously noted. In other words, the proportional valve may be configured to aid in controlling the vacuum flow rate at the outlet port of the ICU ventilation system 14.

Subsequently, at step 66, the gas from the gas supply may be compressed to a desirable level in preparation for pumping into the material transfer pump. The gas may be compressed via use of a pneumatic drive, such as the pneumatic drive 44 (see FIG. 2), in certain embodiments. The compressed gas may be pumped into the material transfer pump to aid in generating a vacuum effect at the outlet port of the ICU ventilation system, as depicted by step 68. Pumping the compressed gas into the material transfer pump may be configured to aid in generating the vacuum effect at the outlet port of the ICU ventilation system. This vacuum effect at the outlet port of the ICU ventilation system may be configured to facilitate sucking the gas out of the lungs of the patient 12. In other words, as indicated by step 70, this sucking out of the gas from the lungs of the patient 12 enables active exhalation of gas from the lungs of the patient 12, as opposed to the typical passive exhalation of gas offered via use of the traditional ICU ventilators.

Furthermore, a pressure of the gas that is input into the patient via the ICU ventilation system may be measured, as indicated by step 72. In one embodiment, the pressure measurement subsystem 28 (see FIG. 1) may be employed to monitor the pressure of the inspiratory gas flow. More particularly, the pressure measurement subsystem 28 may be used to monitor pressure of the gas flow at a proximal location in the patient 12. Based on measurements obtained, it may be desirable to regulate active exhalation of the gas from the lungs of the patient 12. Accordingly, at step 74, a check may be carried out to verify if it is desirable to regulate the active exhalation of gas from the lungs of the patient 12. Further, at step 74, if it is verified that it is desirable to regulate the active exhalation of gas from the lungs of the patient 12, then any desirable changes may be communicated by the ICU ventilation system to the HFOV subsystem. Subsequently, the flow of gas from the gas supply into the material transfer pump may be regulated based on the desirable changes communicated by the ICU ventilation system to the HFOV subsystem. In other words, steps 64, 66 and 68 may be performed. Consequently, the vacuum effect at the outlet port of the ICU ventilation system may be regulated.

The integrated ventilation system and the method for providing high frequency ventilation via use of a high frequency ventilation module described hereinabove dramatically simplify clinical workflow by advantageously allowing a ventilation system, such as the ICU ventilation system, to also provide HFOV to the patient. By integrating the functionality of a separate HFOV system into an ICU ventilation system, clinical workflow may be enhanced, thereby reducing patient discomfort. Further, use of the standalone HFOV subsystem dramatically results in cost reduction and equipment size. Additionally, precious time taken to apply HFOV by switching between the ICU ventilation system and the HFOV system may be saved and patient discomfort may be reduced. Moreover, a seamless transition between normal ventilation and HFOV prevents loss of circuit pressure during the transition. Also, use of more standardized smooth bore ventilation circuits reduces the cost of breathing circuits. In addition, use of the HFOV subsystem may also be configured to provide demand flow during a patient's spontaneous effort.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. An integrated ventilation system, comprising:
a high frequency ventilation module configured to be operationally coupled to an outlet port of a ventilation system, wherein the high frequency ventilation module is configured to aid the ventilation system in performing high frequency ventilation, wherein the high frequency ventilation module comprises a pumping device configured to aid in active exhalation of gas from a patient by creating a vacuum effect at the outlet port of the ventilation system.

2. The integrated ventilation system of claim 1, wherein the pumping device comprises a material transfer pump.

3. The integrated ventilation system of claim 1, wherein the high frequency ventilation module comprises a gas port configured to receive gas to be provided to the pumping device.

4. The integrated ventilation system of claim 3, wherein the high frequency ventilation module comprises:
a proportional valve configured to regulate flow of gas from a gas supply to the pumping device; and
a pneumatic drive configured to compress the gas supplied by the gas supply.

5. The integrated ventilation system of claim 4, further comprising a pressure measuring module configured to monitor pressure of gas at a proximal location in the patient.

6. The integrated ventilation system of claim 5, further comprising a communication and power module, wherein the communication and power module is configured to:
facilitate communication of information between the ventilation system and the high frequency ventilation module; and
provide power to the high frequency ventilation module.

7. The integrated ventilation system of claim 6, wherein the information comprises information regarding pressure of gas monitored at the proximal location in the patient.

8. The integrated ventilation system of claim 7, further comprising control circuitry configured to regulate flow of gas from the gas supply to the pumping device based on the information regarding pressure of gas monitored at the proximal location in the patient.

9. The integrated ventilation system of claim 1, further comprising smooth bore breathing circuits configured to aid in reducing resistance to flow of gas.

10. An integrated ventilation system, comprising:
a ventilation system configured to provide artificial respiration to a patient, said ventilation system comprising at least an inlet port and an outlet port; and
a high frequency ventilation module configured to be operationally coupled to the outlet port of the ventilation system, wherein the high frequency ventilation module comprises a pumping device configured to aid in active exhalation of gas from a patient by creating a vacuum effect at the outlet port of the ventilation system.

11. The integrated ventilation system of claim 10, further comprising a pressure measuring module configured to monitor pressure of gas at a proximal location in the patient.

12. The integrated ventilation system of claim 10, wherein the high frequency ventilation module comprises:
a gas port configured to receive gas to be provided to the pumping device;
a proportional valve configured to regulate flow of gas from the gas supply to the pumping device; and
a pneumatic drive configured to compress the gas supplied by the gas supply.

13. The integrated ventilation system of claim 12, further comprising:
a communication and power module, wherein the communication and power module is configured to:
facilitate communication of information between the ventilation system and the high frequency ventilation module;
provide power to the high frequency ventilation module; and
control circuitry configured to regulate flow of gas from the gas supply to the pumping device.

14. A method comprising:
providing a high frequency ventilation module operationally coupled to an outlet port of a ventilation system, the high frequency ventilation module comprising a pumping device, and
creating a vacuum effect at the outlet port of the ventilation system via the use of the pumping device to aid in active exhalation of gas from a patient.

15. The method of claim 14, wherein creating the vacuum effect at the outlet port of the ventilation system comprises:
regulating flow of gas from a gas supply to the pumping device; and
compressing the gas supplied by the gas supply.

16. The method of claim 15, wherein creating the vacuum effect at the outlet port of the ventilation system further comprises pumping the compressed gas through the pumping device to aid in creating the vacuum effect at the outlet port of the ventilation system.

17. The method of claim 14, further comprising monitoring pressure of gas at a proximal location in the patient.

18. The method of claim 17, further comprising regulating flow of gas from the gas supply to the pumping device based on the pressure of the gas monitored at the proximal location in the patient.

19. The method of claim 14, further comprising providing smooth bore breathing circuits configured to aid in reducing resistance to flow of gas.

\* \* \* \* \*